(12) United States Patent
Shoshtaev et al.

(10) Patent No.: US 12,053,211 B2
(45) Date of Patent: Aug. 6, 2024

(54) POSTERIOR CERVICAL FIXATION SYSTEM

(71) Applicant: NuVasive, Inc., San Diego, CA (US)

(72) Inventors: Eugene Shoshtaev, Del Mar, CA (US); Shaeffer Bannigan, San Diego, CA (US); Michael Brotman, San Diego, CA (US)

(73) Assignee: Nuvasive Inc., Audubon, PA (US)

( * ) Notice: Subject to any disclaimer, the term of this patent is extended or adjusted under 35 U.S.C. 154(b) by 404 days.

(21) Appl. No.: 17/409,746

(22) Filed: Aug. 23, 2021

(65) Prior Publication Data
US 2021/0378717 A1     Dec. 9, 2021

Related U.S. Application Data

(63) Continuation of application No. 16/453,631, filed on Jun. 26, 2019, now Pat. No. 11,123,110, which is a continuation of application No. 15/936,107, filed on Mar. 26, 2018, now Pat. No. 10,368,918, which is a continuation of application No. 15/182,414, filed on Jun. 14, 2016, now Pat. No. 9,956,009, which is a continuation of application No. 13/410,213, filed on Mar. 1, 2012, now Pat. No. 9,387,013.

(Continued)

(51) Int. Cl.
*A61B 17/70*     (2006.01)
*A61B 17/80*     (2006.01)

(52) U.S. Cl.
CPC ...... *A61B 17/7052* (2013.01); *A61B 17/7013* (2013.01); *A61B 17/7037* (2013.01); *A61B 17/7049* (2013.01); *A61B 17/705* (2013.01); *A61B 17/7055* (2013.01); *A61B 17/7056* (2013.01); *A61B 17/7064* (2013.01); *A61B 17/7082* (2013.01); *A61B 17/8061* (2013.01)

(58) Field of Classification Search
CPC .. A61B 17/7058–7059; A61B 17/7007; A61B 17/7064; A61B 17/7076; A61B 17/7082; A61B 17/8875–8894
See application file for complete search history.

(56) References Cited

U.S. PATENT DOCUMENTS

| 5,445,641 | A | * | 8/1995 | Frigg | ............. | A61B 17/88 |
| | | | | | | 606/86 R |
| 9,387,013 | B1 | * | 7/2016 | Shoshtaev | .......... | A61B 17/7055 |

(Continued)

*Primary Examiner* — Eduardo C Robert
*Assistant Examiner* — Michelle C Eckman

(57) ABSTRACT

A posterior cervical fixation system including an occipital plate member, a cross connector, a pair of elongated spinal rods and a plurality of polyaxial screws. The occipital plate member configured for fixing to an occipital bone comprises an aperture to receive a bone anchor member to secure the occipital plate member to the occipital bone and at least one rod clamping element dimensioned to receive at least one spinal rod. The cross connector secures the pair of elongated spinal rods to vertebral bodies. The cross connector includes a pair of collet connectors and a cross bar that is configured to secure the pair of elongated spinal rods in a desired distance. Each polyaxial screw has an anchor head associated with a fastening member. The pair of elongated spinal rods is configured to extend along the vertebral bodies between the occipital plate member and at least one of the polyaxial screws.

4 Claims, 32 Drawing Sheets

Related U.S. Application Data

(60) Provisional application No. 61/555,474, filed on Nov. 3, 2011, provisional application No. 61/450,130, filed on Mar. 8, 2011, provisional application No. 61/447,702, filed on Mar. 1, 2011.

(56) References Cited

U.S. PATENT DOCUMENTS

| | | | | |
|---|---|---|---|---|
| 2003/0149431 A1* | 8/2003 | Varieur | A61B 17/7037 | 606/272 |
| 2003/0153913 A1* | 8/2003 | Altarac | A61B 17/7055 | 606/264 |
| 2004/0127896 A1* | 7/2004 | Lombardo | A61B 17/8042 | 606/296 |
| 2008/0016989 A1* | 1/2008 | Walker | A61B 17/861 | 81/434 |
| 2008/0125781 A1* | 5/2008 | Hoffman | A61B 17/7055 | 606/103 |
| 2008/0177313 A1* | 7/2008 | Lemoine | A61B 17/7055 | 606/250 |
| 2008/0255576 A1* | 10/2008 | Protopsaltis | A61B 17/7091 | 227/176.1 |
| 2010/0069912 A1* | 3/2010 | McCormack | A61B 17/025 | 606/90 |
| 2010/0094351 A1* | 4/2010 | Haggenmaker | A61B 17/7055 | 606/286 |
| 2010/0125299 A1* | 5/2010 | Paul | A61B 17/7044 | 606/280 |
| 2010/0222779 A1* | 9/2010 | Ziemek | A61B 17/7055 | 606/71 |
| 2010/0331852 A1* | 12/2010 | Neubardt | A61B 17/8875 | 81/433 |
| 2011/0130767 A1* | 6/2011 | Watt | B25B 23/06 | 606/104 |
| 2012/0065686 A1* | 3/2012 | Black | A61B 17/7055 | 606/252 |

\* cited by examiner

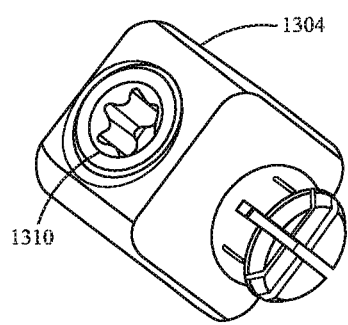
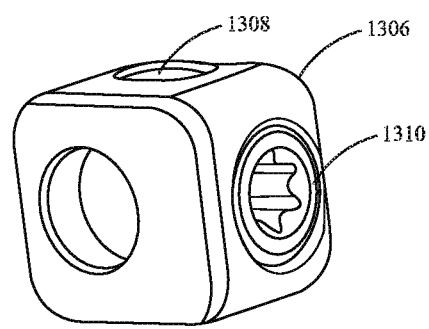
FIG. 23A                    FIG. 23B

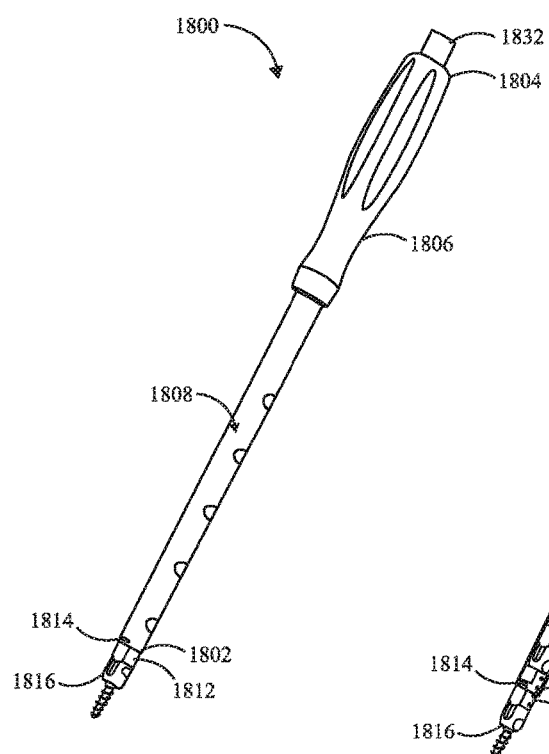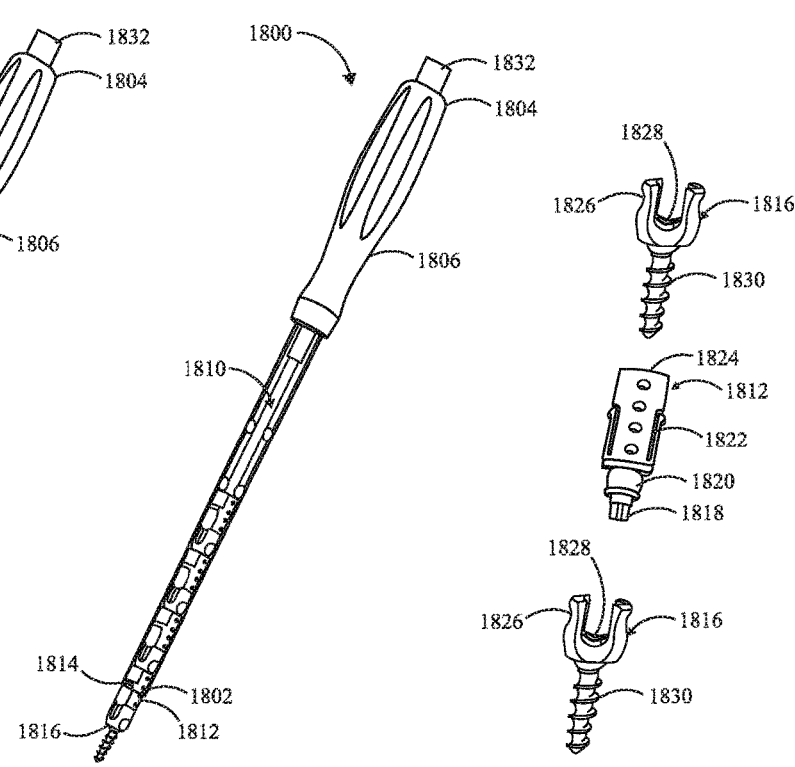
FIG. 33   FIG. 34   FIG. 35

POSTERIOR CERVICAL FIXATION SYSTEM

CROSS REFERENCE TO RELATED APPLICATIONS

This application is a continuation application of U.S. patent application Ser. No. 16/453,631 filed Jun. 26, 2019, which is a continuation of U.S. patent application Ser. No. 15/936,107 filed Mar. 26, 2018, now U.S. Pat. No. 10,368,918, which is a continuation of U.S. patent application Ser. No. 15/182,414 filed Jun. 14, 2016, now U.S. Pat. No. 9,956,009, which is a continuation of U.S. patent application Ser. No. 13/410,213 filed Mar. 1, 2012, now U.S. Pat. No. 9,387,013, which claims the benefit of the filing date of U.S. Provisional Application No. 61/447,702 filed on Mar. 1, 2011, U.S. Provisional Application No. 61/450,130 filed on Mar. 8, 2011, and U.S. Provisional Application No. 61/555,474 filed on Nov. 3, 2011, the entire contents of which are incorporated herein by reference.

FIELD

The present embodiment relates in general to spinal fixation systems and, more particularly, to a posterior cervical fixation system configured for attachment to the posterior part of the human spine from the occipital portion of the human to cervical and/or thoracic vertebrae.

BACKGROUND

The spinal column is a bio-mechanical structure composed primarily of ligaments, muscles, bones, and connective tissue that forms a series of vertebral bodies stacked one atop the other and intervertebral discs between each vertebral body. The spinal column provides support to the body and provides for the transfer of the weight and the bending movements of the head, trunk and arms to the pelvis and legs; complex physiological motion between these parts; and protection of the spinal cord and the nerve roots.

Common spinal column disorders include degenerative disc disease, facet arthritis, and other conditions such as spondylolysis, spondylolisthesis, scoliosis, fractured vertebra, ruptured or slipped discs, tumors, or infections and other disorders caused by abnormalities, disease or trauma. Patients who suffer from one of more of these conditions often experience extreme pain, and can sustain permanent neurologic damage if the conditions are not treated appropriately.

The stabilization of the vertebra and the treatment for above described conditions is often aided by a surgically implanted fixation device which holds the vertebral bodies in proper alignment and reduces the patient's pain and prevents neurologic loss of function. Spinal fixation is a well-known and frequently used medical procedure. Spinal fixation systems are often surgically implanted into a patient to aid in the stabilization of a damaged spine or to aid in the correction of other spinal deformities. Existing systems often use a combination of rods, plates, pedicle screws, bone hooks locking screw assemblies and connectors for fixing the system to the affected vertebrae. The system components may be rigidly locked together in a variety of configurations to promote fusion for a wide variety of patient anatomies.

Posterior fusion and fixation may be the optimal approach for patients in whom the construct requires an extension to the upper cervical or thoracic spine, and to the occiput. Overall, posterior stabilization is generally preferred for posterior and circumferential cervical injuries. Several kinds of posterior fixation systems have been devised. Examples include sublaminar wiring with rod/plate fixation, laminar hook with rod fixation, and pedicle screw with a rod fixation system. However, the sublaminar wiring system has a restriction because the lower cervical laminae are smaller and weaker than upper thoracic vertebrae; and laminar hooks are not preferred because they cannot be fixed in the narrow spinal canal. Alternatively, posterior screw fixation systems provide excellent stability and strength for patients without any external support.

Advancements in posterior cervical fixation have progressed from a wiring procedure to hook and plate-screw systems; and more recently to the versatile rod-screw system.

In some fixation systems, the plates are mounted to the skull with several small screws along the full length and width of the plate. As a result, the spinal rods must be bent in multiple planes away from the vertebrae in order to reach the occipital region. This bending of the rod may potentially weaken the overall assembly, and result in longer operations; and also makes it more difficult to reposition the elements of the stabilization system.

Therefore, there is a need for a posterior cervical fixation system that includes the easy installation of rods which would reduce the risk of implant failure and loss of alignment; and provide for easy adaptation for extension to the occiput or cervical/thoracic spine

SUMMARY

The posterior cervical fixation system comprises a pair of elongated spinal rods, an occipital plate member, a cross connector and a plurality of polyaxial screws. The posterior cervical fixation system of the preferred embodiment is described herein for attachment to the posterior part of the human spine from the occiput to the cervical and/or thoracic vertebrae. The posterior cervical fixation system facilitates securing of an orthopedic rod to the spine/skull.

The occipital plate member is configured for fixing to an occipital bone. The occipital plate member includes at least one aperture, that receives at least one bone anchor member to secure the occipital plate member to the occipital bone and at least one rod clamping element that is dimensioned to receive the spinal rod. Each polyaxial screw includes an anchor head that is associated with a fastening member. The pair of elongated spinal rods includes a first elongated spinal rod and a second elongated spinal rod which is configured to extend along vertebral bodies between the occipital plate member and at least one polyaxial screw.

The cross connector secures the first and second elongated spinal rods to the vertebral bodies of the spine. The cross connector includes a pair of collet connectors and a cross bar which is configured to secure the first and second elongated spinal rods in desired distance. The fastening member of the polyaxial screw is inserted in the vertebral bodies by facing the anchor head upwards to receive the elongated spinal rods. The elongated spinal rods are effectively locked in the anchor head by connecting the cross connector in the anchor head.

One embodiment of the occipital plate member of the posterior cervical fixation system comprises an upper surface and a lower surface, in which the lower surface is configured to contact a portion of the occipital bone. The occipital plate member includes generally a flat main body portion having a first surface, a second surface and a centerline axis. Both first and second surfaces have a recessed portion and an opening and the centerline axis has a plurality of openings. The main body portion further includes a first end in which at least a portion of the first end extends away from the centerline axis and a second end in which at least a portion of the second end extends away from the centerline axis. The occipital plate member is fixed to the occipital bone by inserting a plurality of bone anchor members through the plurality of openings in the centerline axis and each opening on the first and second surfaces of the main body portion.

The openings on the first and second surfaces are fitted with a washer that interfaces with the occipital plate member and the bone anchor member. The occipital plate member further includes a first rotating housing having a lower portion and a hole adaptable to engage with the recessed portion and the opening of the first surface, a second rotating housing having a lower portion and a hole adaptable to engage with the recessed portion and the opening of the second surface.

The occipital plate member further includes a first rod clamping element and a second rod clamping element. The first rod clamping element is dimensioned to couple the occipital plate member to a first elongated spinal rod. Similarly, the second rod clamping element is dimensioned to couple the occipital plate member to a second elongated spinal rod. The first rod clamping element extends laterally from the first end of the main body portion and the second rod clamping element extends laterally from the second end of the main body portion. The first rod clamping element includes a first clamp portion having a rod receiving end and a hole extending therethrough in communication with the rod receiving end and a first body portion having a pin slot therethrough on a body of the first body portion. Similarly, the second rod clamping element includes a second clamp portion having a rod receiving end and a hole extending therethrough in communication with the rod receiving end and a second body portion having a pin slot therethrough on a body of the second body portion.

The occipital plate member further includes a plurality of pins that is coupled to the first and second rotating housings. The pin slots of the first and second rod clamping elements receive the pins and enable each of the rod clamping elements to rotate in medially and laterally within each of the rotating housings to achieve a collapsed state and an expanded state. The occipital plate member further includes a first locking element to lock the first elongated spinal rod within the rod receiving end of the first rod clamping element and a second locking element to lock the second elongated spinal rod within the rod receiving end of the second rod clamping element. The first and second locking elements comprise a set screw.

In order to achieve this locking interaction, the set screws threadedly engage the holes on the first and second clamp portions such that the set screws may be advanced toward the elongated spinal rods until a distal tip of the set screws contacts the elongated spinal rods. A first locking means engages the first rotating housing and the first rod clamping element to the main body portion and a second locking means engages the second rotating housing and the second rod clamping element to the main body portion. Specifically, both the locking means comprise a lock nut which is dimensioned to interlock the first and second rotating housings and the first and second rod clamping elements with the first and second surfaces of the main body portion. The first and second rod clamping elements have generally C-shaped rod-receiving ends to facilitate side loading of the elongated spinal rods.

Yet another embodiment of an occipital plate member is similar to the first embodiment discussed above, but the first and second rod clamping elements have a generally U-shaped rod-receiving ends with threaded side walls extending therethrough in communication with the rod receiving ends respectively, in which the rod receiving ends are dimensioned to face upward. Also, the first and second locking means is a locking screw which is positioned vertically offset from center of the rotating housings. The first and second locking means enables the locking of the first and second rod clamping elements and the first and second rotating housings in a desired position. The openings in the main body portion are angled such that the bone anchor members are guided into the occipital bone at an oblique angle to the transverse axis of the occipital plate member.

Still another embodiment of an occipital plate member is similar to the second embodiment discussed above, but the U-shaped rod-receiving ends with a threaded side walls extending therethrough in communication with the rod receiving ends is attached with rod receiving towers having threaded side walls extending therethrough in communication with the rod receiving towers.

The cross connector forming part of a posterior cervical fixation system includes a first connector, a second connector and a cross bar. The cross bar includes a first end that is surrounded with a first ball spring collar and a second end that is surrounded with a second ball spring collar. The first connector is configured to receive the first elongated spinal rod and is adaptable to directly attach with a first polyaxial screw. Similarly, the second connector is configured to receive a second elongated spinal rod and adaptable to directly attach with a second polyaxial screw.

The first connector includes a first collet head having a recess to receive an anchor head of the first polyaxial screw and a plurality of cutouts to accommodate the first elongated spinal rod, a first clamp having a first spherical pocket to receive the first ball spring collar of the cross bar and a first locking means tightened over the first clamp placed above the first collet head. The first locking means enables a snap-fit engagement of the first connector with the first end of the cross bar and the anchor head. Similarly, the second connector includes a second collet head having a recess to receive an anchor head of the second polyaxial screw and a plurality of cutouts to accommodate the second elongated spinal rod, a second clamp having a second spherical pocket to receive the second ball spring collar of the cross bar, a second locking means tightened over the second clamp placed above the second collet head. The second locking means enables a snap-fit engagement of the second connector with the second end of the cross bar and the anchor head.

The first clamp is attached to the first ball spring collar at the first end of the cross bar and the second clamp is attached to the second ball spring collar at the second end of the cross bar. The first and second spherical pockets receive the first and second ball collars and permit the cross bar to translate in either direction for adjusting to the distance and allow rotational adjustment in the axial plane on both sides of a spinal construct.

The cross bar has the first end that is surrounded with the first ball spring collar and the second end that is surrounded with the second ball spring collar. The first ball spring collar and the second ball spring collar attached on the cross bar allows rotational adjustment to the first and second connectors in an axial plane, the rotational adjustment provides stability to the cross-connector when one polyaxial screw is positioned deeper than the other polyaxial screw on the vertebral bodies. The cross bar translates through the first and second spherical pockets through a conical passage which permits the cross bar to be angularly adjusted relative to the first and second clamps.

A portion of the occipital plate member is configured to contact the occipital bone on the region of a human skull and another portion of the occipital plate member is configured to extend from the occipital plate member to an area that is adjacent to at least one vertebra. The pair of elongated spinal rods is then secured to the occipital plate member. The rods are then extended along the posterior aspects of the patient's cervical and potentially thoracic spine on either side of the spinous processes for a desired distance. Once the rod has been secured to the occipital plate member and polyaxial screws, cross connectors may then be employed to maintain the spinal rods at a desired distance from one another.

An eyelet connector, an adjustable angle occipital rod, a side-loading laminar hook, a facet spacer and an adjustable offset rod-to-rod connector are the forming part of the posterior cervical fixation system. The eyelet connector comprises a rod-receiving element with an open side to allow for rod fixation to the occiput bone. The eyelet connector is fixed to the skull with a bone screw inserted through a screw hole and into an occiput. The adjustable angle occipital rod comprises a first rod portion and a second rod portion which pivot in relation to each other about a hinge. The adjustable angle occipital rod further includes a locking mechanism that includes a first disc and a second disc coupled to the first rod portion and the second rod portion respectively utilizing a set screw. In one embodiment, the set screw has a ratcheted surface which engages a ratcheting washer within a set screw housing of the second rod portion. The side-loading laminar hook includes a hook portion which is dimensioned to hook onto a lamina of a cervical vertebra. The facet spacer is dimensioned to be inserted into a facet joint of a vertebra.

In one embodiment, the first and second elongated spinal rods connected to each other with an adjustable offset rod-to-rod connector. The adjustable offset rod-to-rod connector includes a male portion and a female portion that are coupled such that the portions may rotate with respect to each other. Each portion includes a hole for receiving a rod therethrough and a set screw for locking the adjustable offset rod-to-rod connector to the rods.

A multi-load polyaxial screw driver having a handle, a distal end, an outer shaft, a slot for cartridge tab and an inner shaft can be utilized as a storage compartment for polyaxial screws. The outer shaft of the driver can accommodate a plurality of polyaxial screws in tulip heads with a cartridge coupled to each polyaxial screw.

These and other advantages and features of the present embodiment are described with specificity so as to make the present embodiment understandable to one of ordinary skill in the art.

BRIEF DESCRIPTION OF THE DRAWINGS

Many advantages of the present embodiment will be apparent to those skilled in the art with a reading of this specification in conjunction with the attached drawings, wherein like reference numerals are applied to like elements and wherein:

FIG. 23A is a perspective view of a male portion forming part of the adjustable offset rod-to-rod connector of FIG. 22;

FIG. 23B is a perspective view of a female portion forming part of the adjustable offset rod-to-rod connector of FIG. 22;

FIG. 33 is a perspective view of one embodiment of a multi-load polyaxial screw driver, illustrating particularly an outer shaft accommodated with a plurality of polyaxial screws with a cartridge coupled to each polyaxial screw;

FIG. 34 is a perspective view of the multi-load polyaxial screw driver, of FIG. 33, illustrating particularly an inner shaft drives the plurality of screws and cartridge toward a distal end of the driver; and FIG. 35 is an assembling view of polyaxial screws with cartridge forming part of the multi-load polyaxial screw driver of FIG. 33.

DETAILED DESCRIPTION

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fixation system disclosed herein boasts a variety of inventive features and components that warrant patent protection, both individually and in combination.

Figure 1:
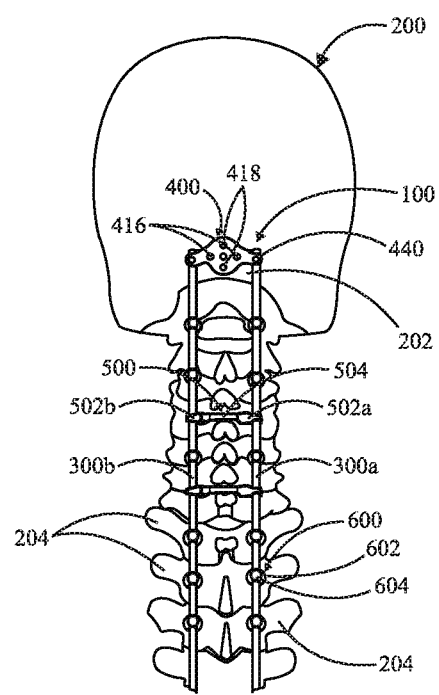
FIG. 1 is a perspective view of an example of a posterior cervical fixation system installed in a spine/skull according to the present embodiment.

FIG. 1 illustrates an example of a posterior cervical fixation system 100 installed in a spine/skull 200 according to the present embodiment. The posterior cervical fixation system 100 comprises a pair of elongated spinal rods 300a, 300b, an occipital plate member 400, a cross connector 500 and a plurality of polyaxial screws 600. The posterior cervical fixation system 100 described herein is for attachment to the posterior part of the human spine from the occiput to the cervical and/or thoracic vertebrae. The posterior cervical fixation system 100 facilitates securing of an orthopedic rod to the spine/skull 200.

The occipital plate member 400 is configured for fixing to an occipital bone 202. The occipital plate member 400 includes at least one aperture 416, 418 (FIG. 2) that receives at least one bone anchor member (not shown) to secure the occipital plate member 400 to the occipital bone 202 and a pair of rod clamping elements 440a, 440b (FIG. 2) dimensioned to receive the first and second elongated spinal rods 300a, 300b respectively. The at least one bone anchor member (not shown) may be at least one of a bone screw, nail, pin or hook. Each polyaxial screw 600 includes an anchor head 602 associated with a fastening member (not shown). The pair of elongated spinal rods includes a first elongated spinal rod 300a and a second elongated spinal rod 300b which is configured to extend along vertebral bodies 204 between the occipital plate member 400 and at least one polyaxial screw 600. The first elongated spinal rod 300a may be of different diameter than the second elongated spinal rod 300b.

Figure 5:
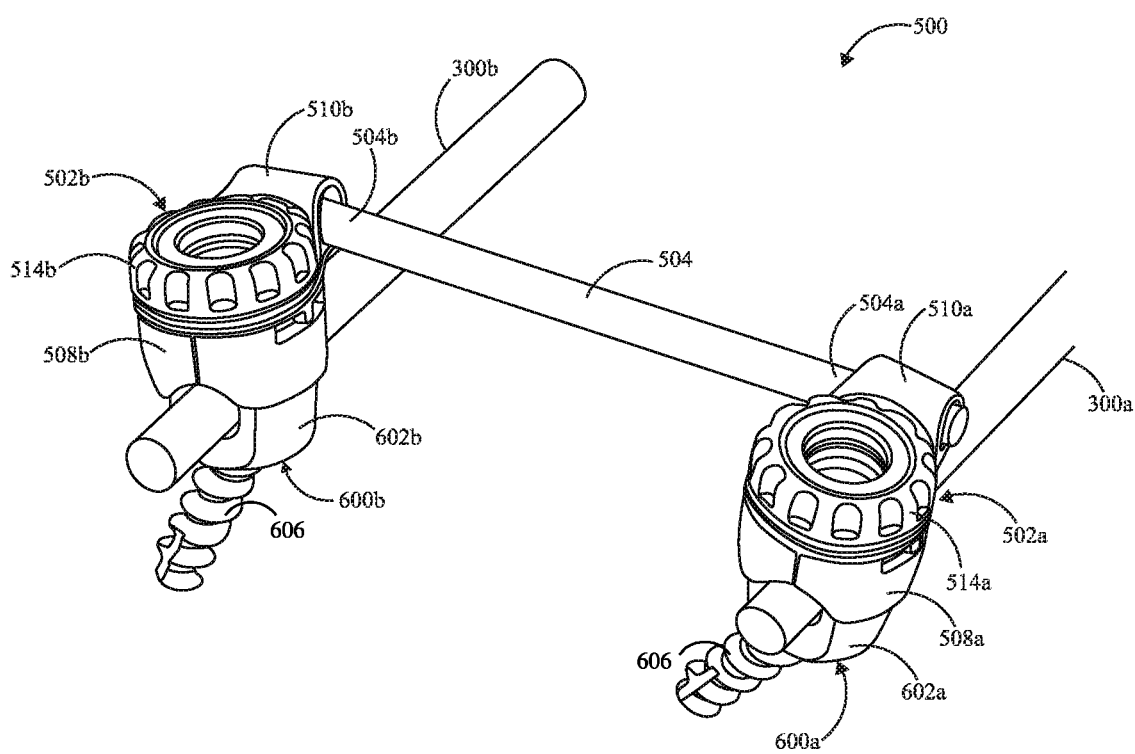
FIG. 5 is a perspective view of a cross connector engaged with the pair of elongated spinal rods forming part of the posterior cervical fixation system of FIG. 1.

The cross connector 500 secures the first and second elongated spinal rods 300a, 300b to the vertebral bodies 204 of the spine. The cross connector 500 includes a pair of collet connectors 502a, 502b (FIG. 5) and a cross bar 504 which is configured to secure the first and second elongated spinal rods 300a, 300b in desired distance. The fastening member 606 of the polyaxial screw 600 is inserted in the vertebral bodies 204 by facing the anchor head 602 upwards to receive the first and second elongated spinal rods 300a, 300b. The first and second elongated spinal rods 300a, 300b are effectively locked in the anchor head 602 by connecting the cross connector 500 to the anchor head 602. The anchor head 602 may include a recess 604 that is adapted to cooperate with a driver (not shown) used to lock the fastening member 606 of the polyaxial screw 600 into the vertebral bodies 204. By way of example only, the recess 604 is shown as a hex-head shaped recess for receiving a hex-head driver. The anchor head 602 is generally spherical in shape and dimensioned to engage with the cross connector 500. Although shown and described by way of example as a polyaxial screw 600, it is including but not limited to a screw, nail, hook, pin, staple, tack, and/or suture. Any or all of these elements may be made of a biologically inert material; preferably any metal customarily used for surgical devices, such as for example titanium or stainless steel.

Figure 2:
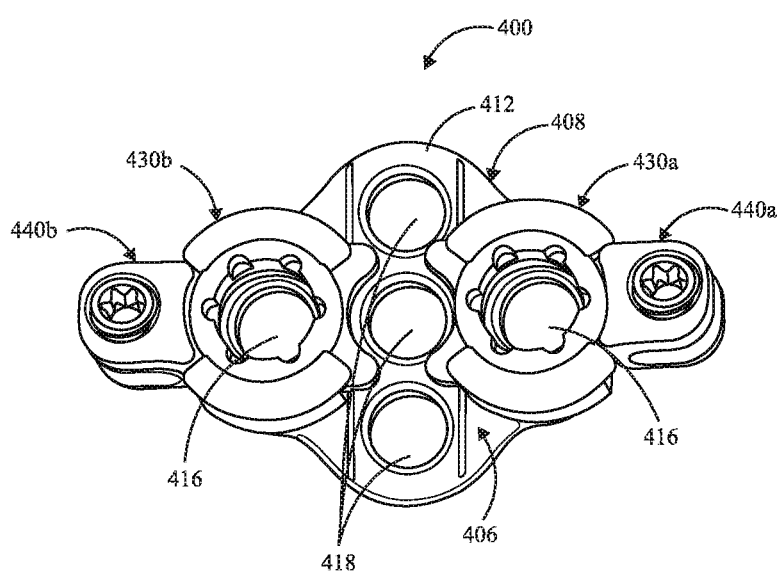
FIG. 2 is a front perspective view of an occipital plate member forming part of the posterior cervical fixation system of FIG. 1 in a collapsed state.
Figure 3:
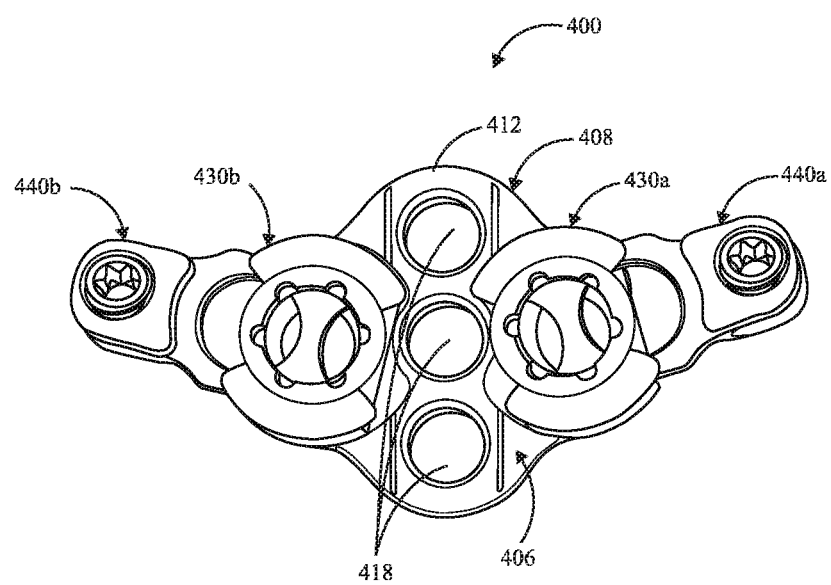
FIG. 3 is a front perspective view of an occipital plate member forming part of the posterior cervical fixation system of FIG. 1 in an expanded state.
Figure 4:
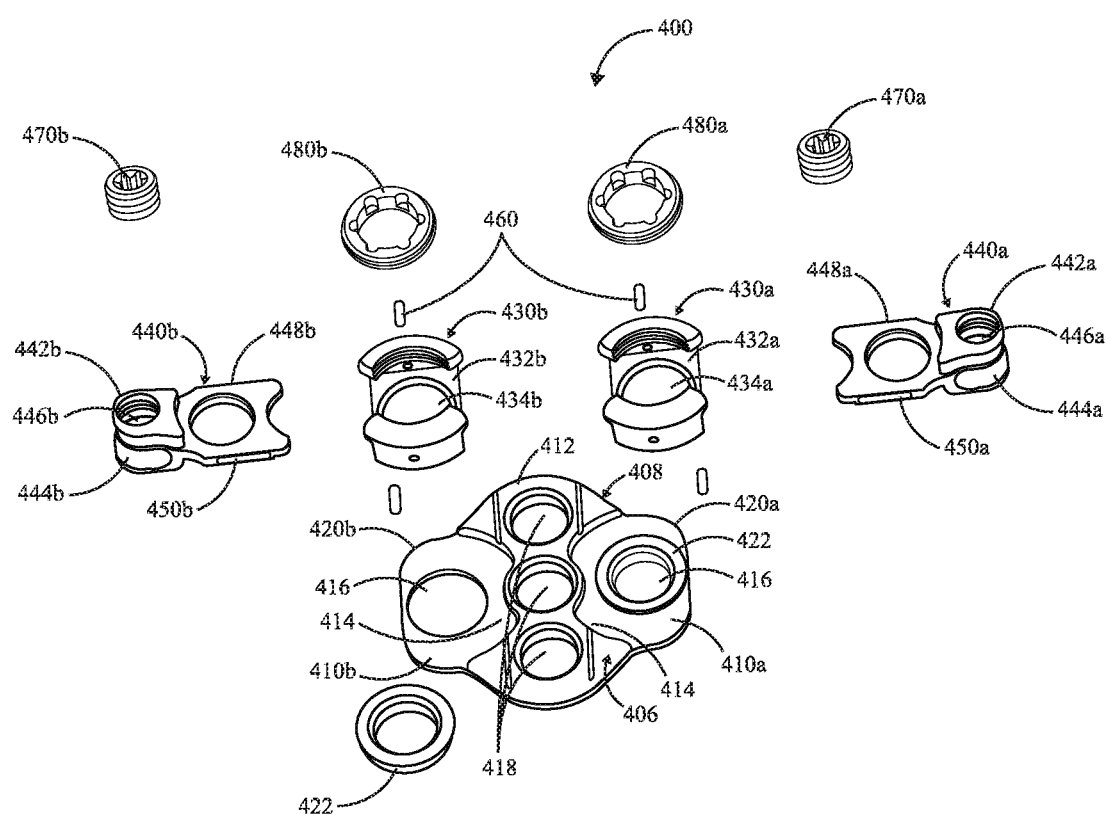
FIG. 4 is an exploded view of the occipital plate member of FIG. 2.

Referring to FIGS. 2-4, the occipital plate member 400 of the posterior cervical fixation system 100 comprises an upper surface 406 and a lower surface (not shown), in which the lower surface (not shown) is configured to contact a portion of the occipital bone 202. The occipital plate member 400 includes a generally flat main body portion 408 having a first surface 410a, a second surface 410b and a centerline axis 412. Both first and second surfaces 410a, 410b have a recessed portion 414 and an opening 416 and the centerline axis 412 has a plurality of openings 418. As an example, the occipital plate member 400 shown in FIGS. 2-4 are provided with five openings, with three of the openings 418 aligned along the centerline axis 412 and additional two openings 416 on either first and second surfaces 410a, 410b of the main body portion 408. These openings 416, 418 may extend through the occipital plate member 400 at an angle such that the bone anchor members (not shown) are guided into the occipital bone 202 at an oblique angle to the transverse axis of the occipital plate member 400. The main body portion 408 further includes a first end 420a in which at least a portion of the first end 420a extends away from the centerline axis 412 and a second end 420b in which at least a portion of the second end 420b extends away from the centerline axis 412. The occipital plate member 400 is fixed to the occipital bone 202 by inserting a plurality of bone anchor members (not shown) through the plurality of openings 418 in the centerline axis and each opening 416 on the first and second surfaces 410a, 410b of the main body portion 408.

The openings 416 on the first and second surfaces 410a, 410b are fitted with a washer 422 that interfaces with the occipital plate member 400 and the bone anchor member (not shown). The occipital plate member 400 further includes a first rotating housing 430a having a lower portion 432a and a hole 434a adaptable to engage with the recessed portion 414 and the opening 416 of the first surface 410a, a second rotating housing 430b having a lower portion 432b and a hole 434b adaptable to engage with the recessed portion 414 and the opening 416 of the second surface 410b. The first and second housings 430a, 430b are able to freely rotate within the recessed portions of the first and second surfaces until a locking means 480a, 480b is deployed to lock the rotating housings 430a, 430b in a desired position.

The occipital plate member 400 further includes a first rod clamping element 440a and a second rod clamping element 440b. The first rod clamping element 440a is dimensioned to couple the occipital plate member 400 to a first elongated spinal rod 300a. Similarly, the second rod clamping element 440b is dimensioned to couple the occipital plate member 400 to a second elongated spinal rod 300b. The first rod clamping element 440a extends laterally from the first end 420a of the main body portion 408 and the second rod clamping element 440b extends laterally from the second end 420b of the main body portion 408. The first rod clamping element 440a includes a first clamp portion 442a having a rod receiving end 444a and a hole 446a extending therethrough in communication with the rod receiving end 444a and a first body portion 448a having a pin slot 450a therethrough on a body of the first body portion 448a. Similarly, the second rod clamping element 440b includes a second clamp portion 442b having a rod receiving end 444b and a hole 446b extending therethrough in communication with the rod receiving end 444b and a second body portion 448b having a pin slot 450b therethrough on a body of the second body portion 448b.

The occipital plate member 400 further includes a plurality of pins 460 that is coupled to the first and second rotating housings 430a, 430b. The pin slots 450a, 450b of the first and second rod clamping elements 440a, 440b receive the pins 460 and enable each of the rod clamping elements 440a, 440b to translate medially and laterally within each of the rotating housings 430a, 430b to achieve a collapsed state (FIG. 2) and an expanded state (FIG. 3). The occipital plate member 400 further includes a first locking element 470a to lock the first elongated spinal rod 300a within the rod receiving end 444a of the first rod clamping element 440a and a second locking element 470b to lock the second elongated spinal rod 300b within the rod receiving end 444b of the second rod clamping element 440b. The first and second locking elements 470a, 470b may comprise, for example, a set screw. According to the embodiment shown in FIGS. 2-4, in order to achieve this locking interaction, the set screws 470a, 470b threadedly engage the holes 446a, 446b on the first and second clamp portions 442a, 442b such that the set screws 470a, 470b may be advanced toward the elongated spinal rods 300a, 300b until a distal tip of the set screws 470a, 470b contacts the elongated spinal rods 300a, 300b. A first locking means 480a engages the first rotating housing 430a and the first rod clamping element 440a to the first surface 410a of the main body portion 408 and a second locking means 480b engages the second rotating housing 430b and the second rod clamping element 440b to the second surface 410b of the main body portion 408. According to the exemplary embodiment shown in FIGS. 2-4, both the locking means 480a, 480b comprise a lock nut which is dimensioned to lock the first and second rotating housings 430a, 430b and the first and second rod clamping elements 440a, 440b with the first and second surfaces 410a, 410b of the main body portion 408 when the first and second rotating housings 430a, 430b and first and second rod clamping elements 440a, 440b are in a desired position.

The first and second rod clamping elements 440a, 440b have a generally C-shaped rod-receiving ends 450a, 450b for facilitating the side-loading of the first and second elongated spinal rods 300a, 300b therethrough. The occipital plate member 400 may be provided in any size suitable for any particular patient. The bone anchor members (not shown) may be provided having any diameter and length dimension suitable for implantation into a patient's skull.

Figure 6:
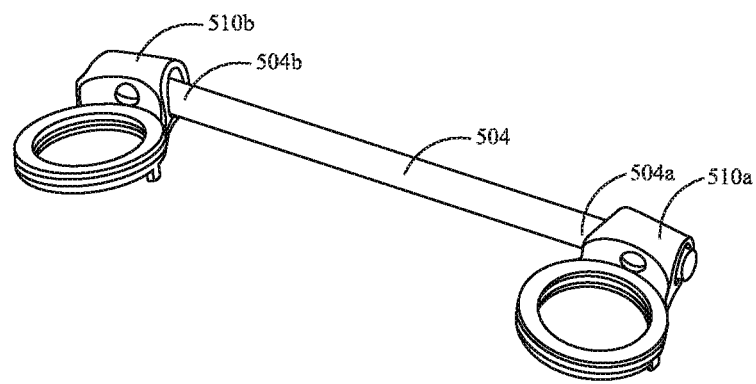
FIG. 6 is a perspective view of a cross bar engaged with a first clamp and a second clamp on either end thereof forming part of the cross connector of FIG. 5.
Figure 7:
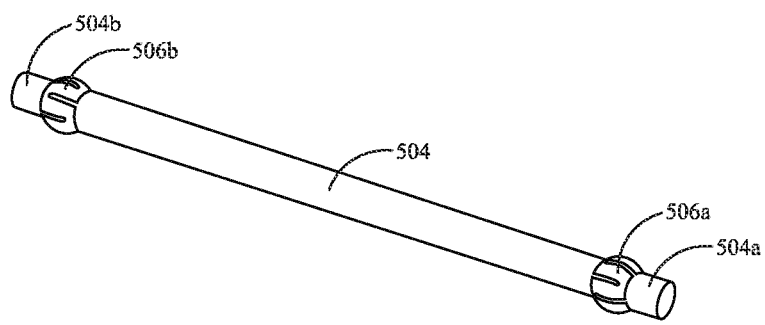
FIG. 7 is a perspective view of a cross bar surrounded with a pair of ball spring collar forming part of the cross connector of FIG. 5.

FIGS. 5-9 illustrate one of embodiment of a cross connector 500 and its associated components forming part of a posterior cervical fixation system 100. The cross connector 500 further includes a first connector 502a, a second connector 502b and a cross bar 504. The cross bar 504 includes a first end 504a that is surrounded with a first ball spring collar 506a (FIG. 7) and a second end 504b that is surrounded with a second ball spring collar 506b (FIG. 7). The first connector 502a is configured to receive the first elongated spinal rod 300a and adaptable to directly attach with a first polyaxial screw 600a. Similarly, the second connector 502b is configured to receive a second elongated spinal rod 300b and adaptable to directly attach with a second polyaxial screw 600b.

The first connector 502a includes a first collet head 508a having a recess (not shown) to receive an anchor head 602a of the first polyaxial screw 600a and a plurality of cutouts (not shown) to accommodate the first elongated spinal rod 300a, a first clamp 510a having a first spherical pocket 512a to receive the first ball spring collar 506a of the cross bar 504 and a first locking means 514a tightened over the first clamp 510a placed above the first collet head 508a. The first locking means 514a enables a snap-fit engagement of the first connector 502a with the first end 504a of the cross bar 504 and the anchor head 602a. Similarly, the second connector 502b includes a second collet head 508b having a recess (not shown) to receive an anchor head 602b of the second polyaxial screw 600b and a plurality of cutouts (not shown) to accommodate the second elongated spinal rod 300b, a second clamp 510b having a second spherical pocket 512b to receive the second ball spring collar 506b of the cross bar 504, a second locking means 514b tightened over the second clamp 510b placed above the second collet head 508b. The second locking means 514b enables a snap-fit engagement of the second connector 502b with the second end 504b of the cross bar 504 and the anchor head 602b.

As shown in FIG. 6, the first clamp 510a attached to the first ball spring collar 506a at the first end 504a of the cross bar 504 and the second clamp 510a attached to the second ball spring collar 506b at the second end 504b of the cross bar 504. The first and second spherical pockets 512a, 512b receive the first and second ball collars 506a, 506b and permit the cross bar 504 to translate in either direction for adjusting to the distance and allow rotational adjustment in the axial plane on both sides of a spinal construct.

Figures 8A, 8B:
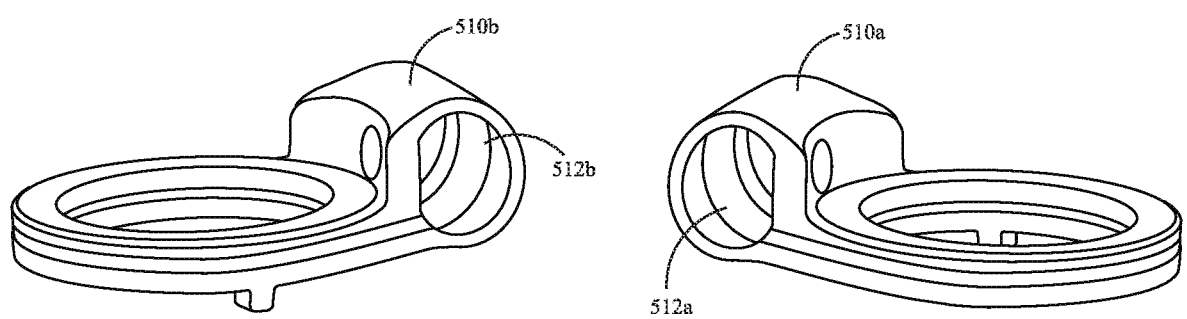
FIG. 8A is a side perspective view of a first clamp of FIG. 6.
FIG. 8B is a side perspective view of a second clamp of FIG. 6.
Figure 9:
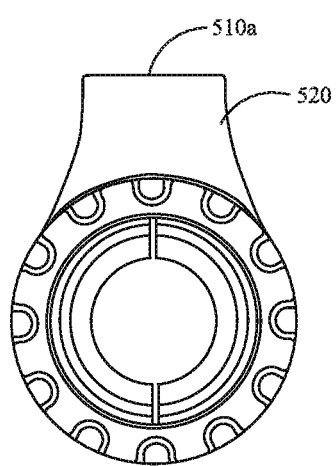
FIG. 9 is a plan view of a clamp of FIG. 6.

As shown in FIG. 7, the cross bar 504 has the first end 504a that is surrounded with the first ball spring collar 506a and the second end 504b that is surrounded with the second ball spring collar 506b. The first and the second ball spring collars 506a, 506b attached on the cross bar 504 allows rotational adjustment to the first and second connectors 502a, 502b in an axial plane, the rotational adjustment provides stability to the cross-connector 500 when one polyaxial screw 600a is positioned deeper than the other polyaxial screw 600b on the vertebral bodies. As shown in FIGS. 8A-9, the cross bar 504 translates through the first and second spherical pockets 512a, 512b through a conical passage 520. The conical passage 520 is larger than the diameter of the cross bar 504 and permits the cross bar 504 to be angularly adjusted relative to the first and second clamps 510a, 510b. The cross bar 500 may be provided in any length suitable for extending between the first and second elongated spinal rods 300a, 300b.

The elongated spinal rods 300a, 300b extend along the posterior aspects of the patient's cervical and potentially thoracic spine on either side of the spinous processes for a desired distance. Any combination of anchor elements, including polyaxial screws and/or laminar hooks as described above may be used to secure the rods to the cervical and/or thoracic vertebrae. Any combination of anchor elements, including bone anchors and/or locking screws as described above may be used to secure the occipital plate to the occipital bone 202. Once the elongated spinal rods 300a, 300b have been secured to the occipital plate member 400 and polyaxial screws 600, cross connectors 500 may then be employed to maintain the elongated spinal rods 300a, 300b at a desired distance from one another.

Figure 10:
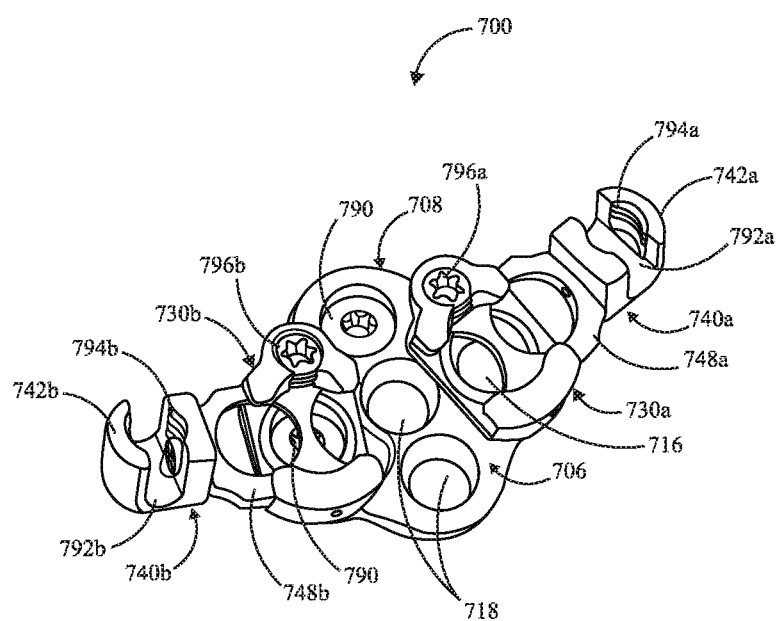
FIG. 10 is a top perspective view of an alternate embodiment of the occipital plate member of FIG. 4 in an expanded state.
Figure 11:
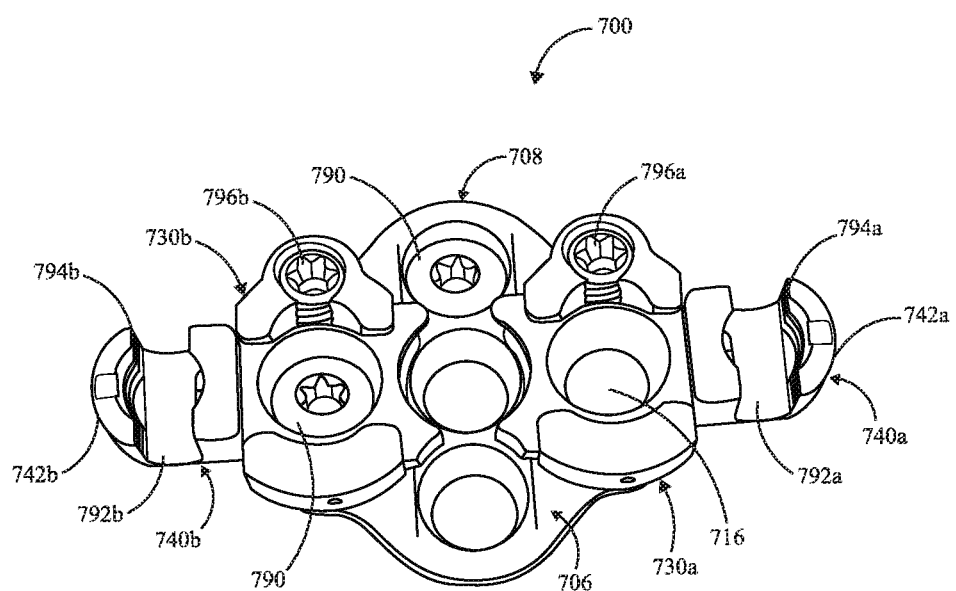
FIG. 11 is a top perspective view of an alternate embodiment of the occipital plate member of FIG. 4 in a collapsed state.

FIGS. 10 and 11 illustrate an alternative embodiment of the occipital plate of FIG. 2. FIG. 10 depicts an occipital plate member attached with U-shaped rod receiving elements in its expanded state. FIG. 11 depicts an occipital plate member attached with U-shaped rod receiving elements in its collapsed state. The occipital plate member 700 in this embodiment is similar structurally and functionally to the embodiment described above, with a difference in that the first and second rod clamping elements 740a, 740b have a generally U-shaped rod-receiving ends 792a, 792b with a threaded side walls 794a, 794b extending therethrough in communication with the rod receiving ends 792a, 792b respectively, in which the rod receiving ends 792a, 792b are dimensioned to face upward. Also, a first locking means 796a and a second locking means 796b are locking screws which are positioned vertically offset from center of a first rotating housing 730a and a second rotating housing 730b respectively. The first and second locking means 796a, 796b enables the locking of the first rod clamping element 740a and the second rod clamping element 740b with the first and second rotating housings 730a, 730b in a desired position. The openings 716, 718 in the main body portion 708 are angled such that the bone anchor members 790 are guided into the occipital bone 202 at an oblique angle to the transverse axis of the occipital plate member 700. More particularly, the illustrated embodiment is similar in all other respects to the preferred embodiment described above, and as such similar components and features are numbered similarly, except in the 700s rather than the 400s.

The occipital plate member 700 has an upper surface 706 and a lower surface (not shown), in which the lower surface (not shown) is configured to contact a portion of the occipital bone 202. The occipital plate member 700 includes a main body portion 708 having a first surface, a second surface and a centerline axis. Both the first and second surfaces have a recessed portion and an opening 716 and the centerline axis has a plurality of openings 718. The main body portion 708 further includes a first end and a second end, in which at least a portion of the first and second ends extends away from the centerline axis. The occipital plate member 700 is fixed to the occipital bone 202 by inserting a plurality of bone anchor members 790 through the plurality of openings 718 in the centerline axis and the opening 716 on the first and second surfaces of the main body portion 708.

The occipital plate member 700 further includes a first rotating housing 730a having a lower portion and a hole adaptable to engage with the recessed portion and the opening 716 of the first surface of the main body portion 708, and a second rotating housing 730b having a lower portion and a hole adaptable to engage with the recessed portion and the opening 716 of the second surface of the main body portion 708. The first and second housings 730a, 730b are able to freely rotate within the recessed portions of the first and second surfaces until a locking means 796a, 796b is deployed to lock the rotating housings 730a, 730b in a desired position.

The occipital plate member 700 further includes a first rod clamping element 740a and a second rod clamping element 740b. The first rod clamping element 740a is dimensioned to couple the occipital plate member 700 to the first elongated spinal rod 300a. Similarly, the second rod clamping element 740b is dimensioned to couple the occipital plate member 700 to the second elongated spinal rod 300b. The first and second rod clamping elements 740a, 740b extend laterally from the first end and second end of the main body portion 708 respectively. The first rod clamping element 740a includes a first clamp portion 742a having the rod receiving end 792a and the threaded side wall 794a extending therethrough in communication with the rod receiving end 792a and a first body portion 748a having a pin slot therethrough on a body of the first body portion 748a. Similarly, the second rod clamping element 740b includes a second clamp portion 742b having the rod receiving end 792b and the threaded side wall 794b extending therethrough in communication with the rod receiving end 792a and a second body portion 748b having a pin slot therethrough on a body of the second body portion 748b.

The occipital plate member 700 further includes a plurality of pins coupled to the first and second rotating housings 730a, 730b. The pin slots of first and second rod clamping elements 740a, 740b receive the pins and enable the first and second rod clamping elements 740a, 740b to translate medially and laterally within the first and second rotating housings 730a, 730b to achieve a collapsed state (FIG. 11) and an expanded state (FIG. 10). The occipital plate member 700 further includes a first locking element (not shown) to lock the first elongated spinal rod 300a within the rod receiving end 744a of the first rod clamping element 740a and a second locking element (not shown) to lock the second elongated spinal rod 300b within the rod receiving end 744b of the second rod clamping element 740b. The first and second locking elements (not shown) may comprise, for example, a set screw.

The first locking means 796a engages the first rotating housing 730a and the first rod clamping element 740a to the main body portion 708 and the second locking means 796b engages the second rotating housing 730b and the second rod clamping element 740b to the main body portion 708. Deploying the first and second locking means 796a, 796b urges the rotating housings 730a, 730b against the top surface 706 of the plate, thereby locking the rotating housings 730a, 730b and rod clamping elements 740a, 740b in a desired position.

Figure 12:
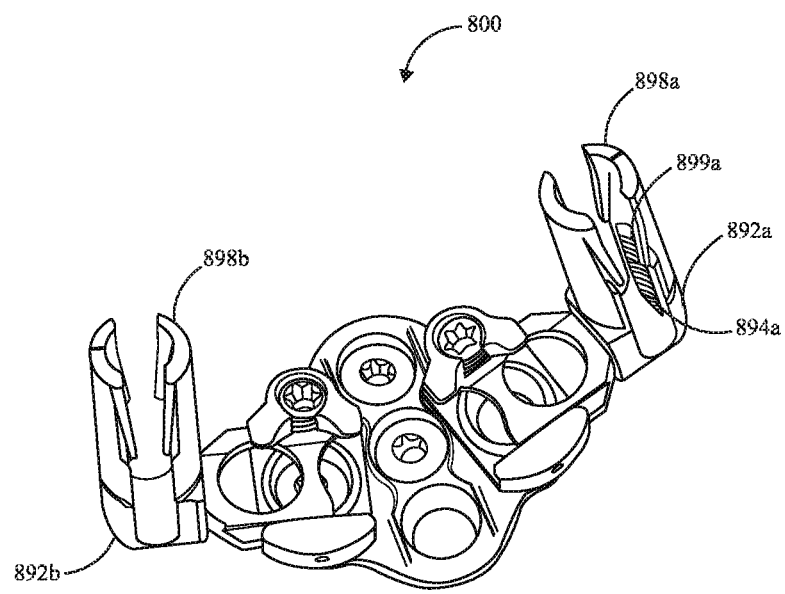
FIG. 12 is a top perspective view of an alternate embodiment of the occipital plate member of FIG. 10.
Figure 13:
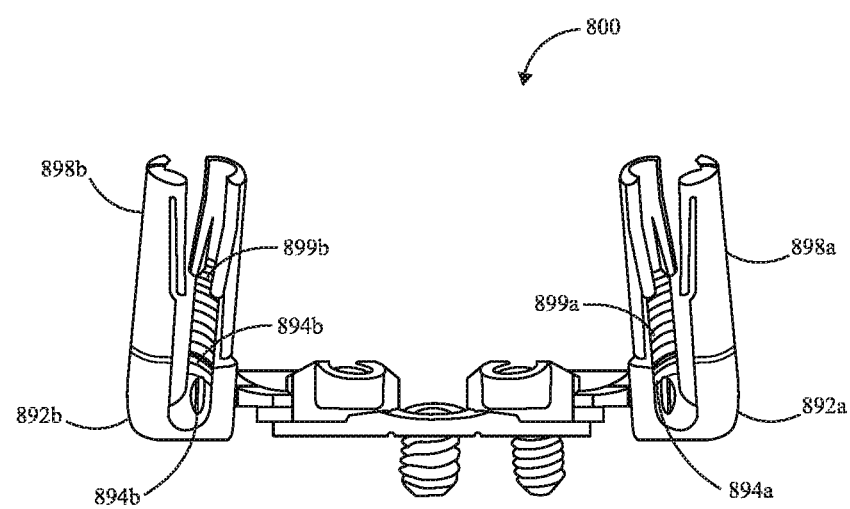
FIG. 13 is a side perspective view of an alternate embodiment of the occipital plate member of FIG. 11.

FIGS. 12 and 13 illustrate an alternative embodiment of the occipital plate member of FIGS. 10 and 11 in an expanded state and a collapsed state. The occipital plate member 800 in this embodiment is similar structurally and functionally to the embodiment described above, with a difference in that the U-shaped rod-receiving ends 892a, 892b with a threaded side walls 894a, 894b extending therethrough in communication with the rod receiving ends 892a, 892b that is attached with rod receiving towers 898a, 898b having a threaded side walls 899a, 899a extending therethrough in communication with the rod receiving towers 898a, 898b. More particularly, the illustrated embodiment is similar in all other respects to the embodiment in FIGS. 10 and 11, and as such similar components and features are numbered similarly, except in the 800s rather than the 700s.

Figure 14:
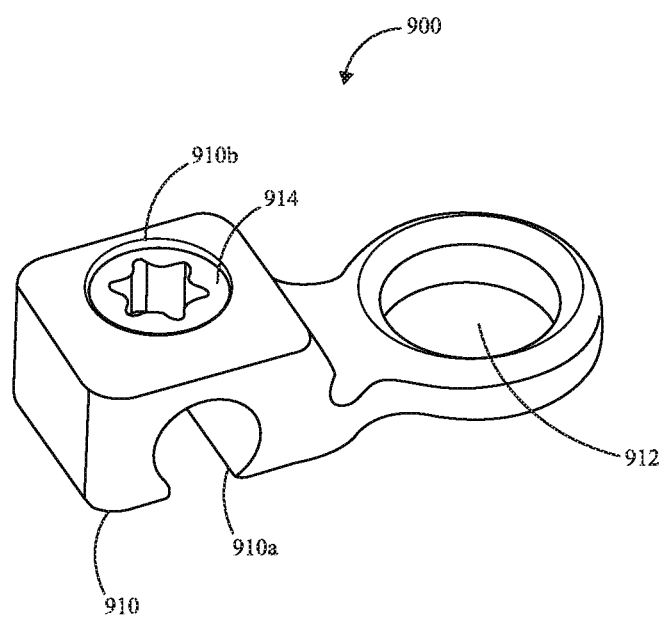
FIG. 14 is a perspective view of an eyelet connector forming part of the posterior cervical fixation system of FIG. 1 for fixing a spinal rod to human occiput.

FIG. 14 illustrates one example of an eyelet connector 900 forming part of the posterior cervical fixation system 100. The eyelet connector 900 is provided for fixing the elongated spinal rods 300a, 300b to human occiput. The eyelet connector 900 comprises a rod receiving element 910 and a screw hole 912. The rod receiving element 910 having an open side 910a facing the occipital bone that allows the elongated spinal rods 300a, 300b to pass through and a set screw hole 910b for the spinal rod fixation to the occiput with a minimal profile. The elongated spinal rods 300a, 300b are locked with the occipital bone 202 by inserting a set screw 914 through the set screw hole 910b. The eyelet connector 900 is fixed to the skull with a bone screw (not shown) inserted through the screw hole 912 and into the occiput.

Figure 15:
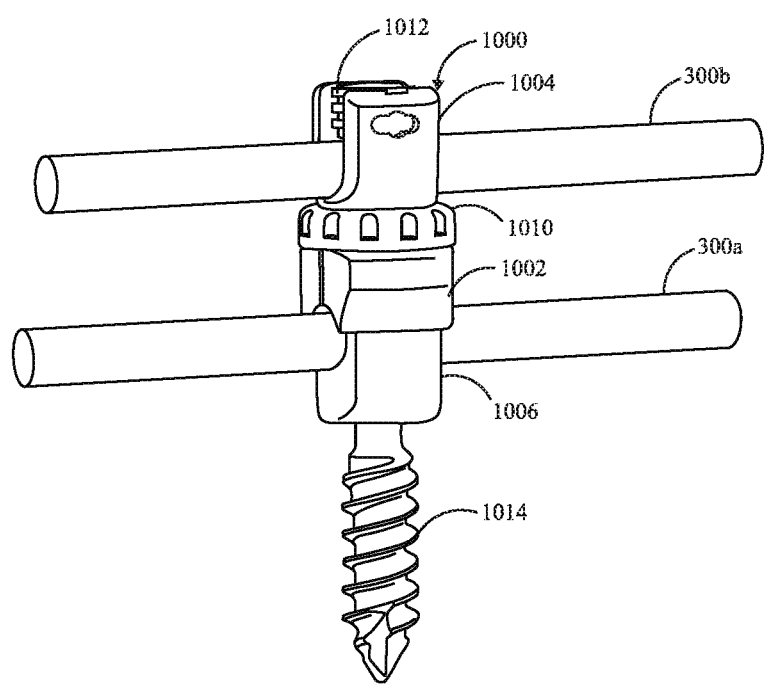
FIG. 15 is a perspective view of an example of a collet and anchor head connector forming part of a posterior cervical fixation system of FIG. 1 for top loading a second spinal rod.
Figure 16:
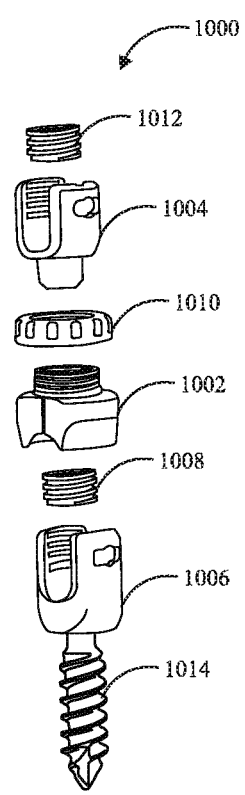
FIG. 16 is an exploded perspective view of a collet and anchor head connector of FIG. 15.

FIGS. 15 and 16 illustrate an example of a collet and anchor head connector 1000 forming part of a posterior cervical fixation system for top loading a second elongated spinal rod. The collet and anchor head connector 1000 is engaged with a first elongated spinal rod 300a and top loaded with a second elongated spinal rod 300b as shown in FIG. 15. In each of the presented embodiments, the second elongated spinal rod 300b is shown as co-linear with the first elongated spinal rod 300a. The first and second elongated spinal rods 300a, 300b are secured into the bone with a cross connector 500 and an occipital plate member 400 (FIGS. 1 and 10). According to this example, shown in FIGS. 15 and 16, a collet connector 1002 and a second anchor head 1004 may also be oriented to allow the second elongated spinal rod 300b to be positioned transverse to the first elongated spinal rod 300a. The collet connector 1002 may be coupled to a first anchor head 1006 with a first set screw 1008 and a locking cap 1010 is threaded onto the collet connector 1002. The first set screw 1008 is received within apertures (not shown) in the collet connector 1002 and the locking cap 1010. The second elongated spinal rod 300b may be secured within the second anchor head 1004 with a second set screw 1012. The second anchor head 1004 is inserted into the locking cap 1010 and engaged with the collet connector 1002. A screw shank 1014 attached with the first anchor head 1006 is inserted into the bone.

Figure 17:
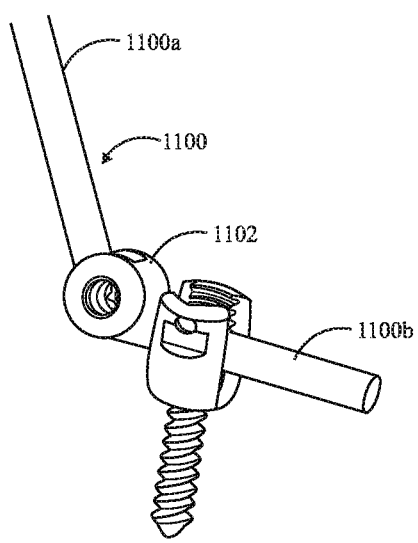
FIG. 17 is a perspective view of an adjustable angle occipital rod attached to a polyaxial screw forming part of the posterior cervical fixation system of FIG. 1.
Figure 18:
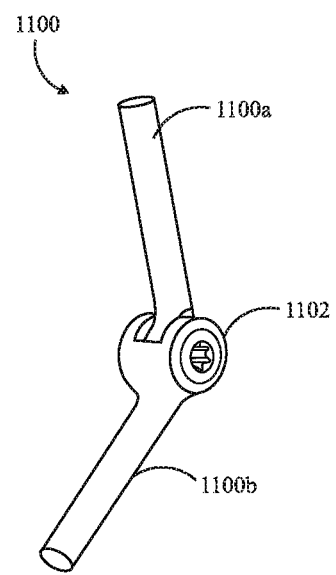
FIG. 18 is a perspective view of the adjustable angle occipital rod of FIG. 17.
Figure 19A:
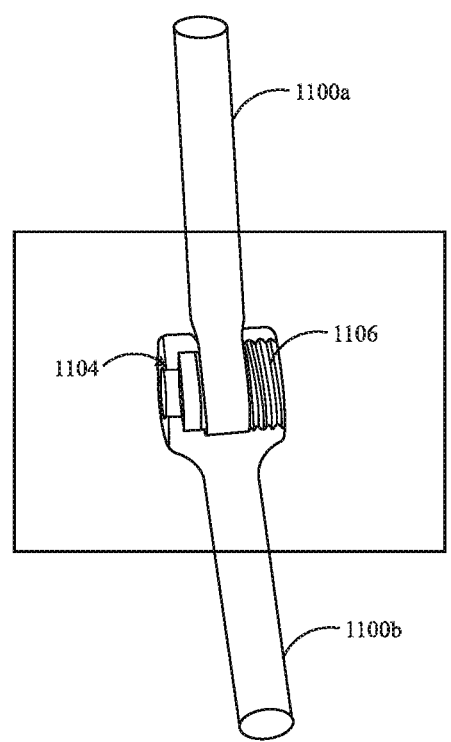
FIG. 19A is a partial sectional view of the adjustable angle occipital rod of FIG. 17, detailing a locking mechanism.
Figure 19B:
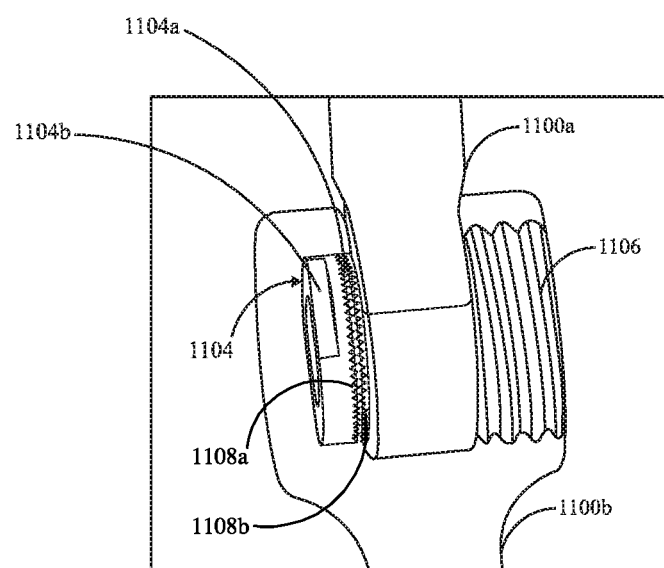
FIG. 19B is a sectional close-up view of the locking mechanism in the adjustable angle occipital rod according to FIG. 19A.

FIGS. 17-19B illustrate an adjustable angle occipital rod forming part of a posterior cervical fixation system of FIG. 1. FIG. 17 depicts an adjustable angle occipital rod attached to a polyaxial screw. FIG. 18 depicts an adjustable angle occipital rod illustrating a hinge. FIGS. 19A and 19B depict an adjustable angle occipital rod that includes a locking mechanism. The adjustable angle occipital rod 1100 comprises a first rod portion 1100a and a second rod portion 1100b that pivot in relation to each other about a hinge 1102. The first and second rods 1100a, 1100b further comprises a locking mechanism 1104 therebetween. The locking mechanism 1104 includes a first disc 1104a coupled to the first rod portion 1100a and a second disc 1104b coupled to the second rod portion 1100b. The first and second discs 1104a, 1104b have an engagement surface (1108a) that faces the engagement surface (1108b) of the other disc, the engagement surfaces 1108a, 1108b having a plurality of teeth to allow the first and second rods 1100a, 1100b to be rotated and locked in discrete increments of angulation relative to each other. The first and second rod portions 1100a, 1100b are engaged together with a set screw 1106. When the set screw 1106 is in the unlocked position, the first and second rod portions 1100a, 1100b can rotate freely about the hinge 1002. When the first and second rod portions 1100a, 1100b are in the desired position, the set screw 1106 can be turned to the locked position, urging the engagement surfaces 1108a, 1108b of the first and second discs 1104a, 1104b in contact with each other to prevent movement of the first and second rod portions 1100a, 1100b.

Figure 20:
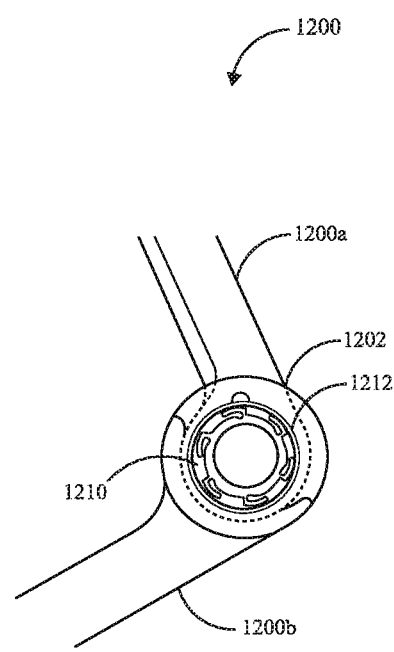
FIG. 20 is a partial sectional view of an alternate embodiment of an adjustable angle occipital rod of FIG. 19A, detailing a set screw housing.
Figure 21:
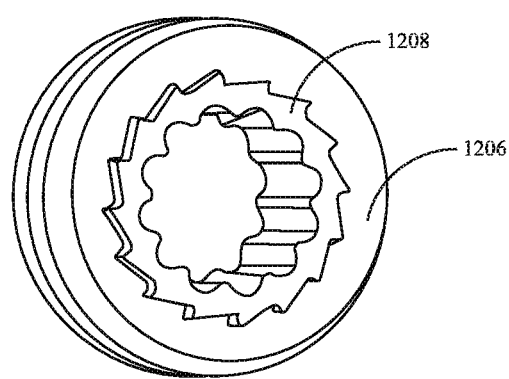
FIG. 21 is an enlarged view of a set screw forming part of an adjustable angle occipital rod of FIG. 20.

FIGS. 20 and 21 illustrate an alternative embodiment of an adjustable angle occipital rod of FIGS. 17-19B. FIG. 20 depicts an adjustable angle occipital rod attached with screw housing. FIG. 21 depicts a set screw forming part of an adjustable angle occipital rod of FIG. 20. The adjustable angle occipital rod 1200 in this embodiment is similar structurally and functionally to the embodiment described above, with a difference in that a first rod portion 1200a and a second rod portion 1200b that pivot in relation to each other about a hinge 1202. The set screw 1206 has a ratcheted surface 1208 that engages a ratcheting washer 1210 is secured within set screw housing 1212 of the second rod portion 1200b. The interaction of the ratcheting surface 1208 on the set screw 1206 with the ratcheting washer 1210 limits the turning and tightening of the set screw 1206 to only one direction. More particularly, the illustrated embodiment is similar in all other respects to the preferred embodiment described above, and as such similar components and features are numbered similarly, except in the 1200s rather than the 1100s.

Figure 22:
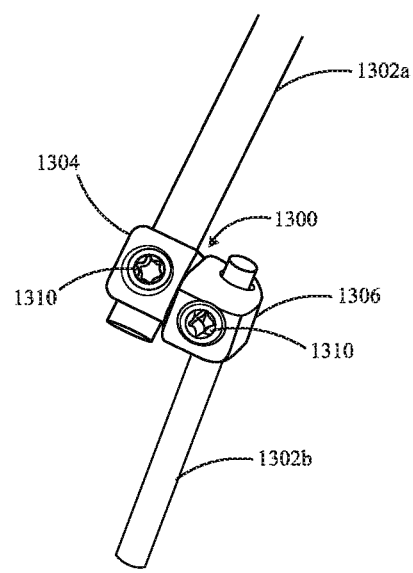
FIG. 22 is a perspective view of an adjustable offset rod-to-rod connector engaged with a pair of elongated spinal rods forming part of the posterior cervical fixation system of FIG. 1.

FIGS. 22-23B demonstrate one embodiment of an adjustable offset rod-to-rod connector. FIG. 22 depicts the adjustable offset rod-to-rod connector engaged with a pair of elongated spinal rods. FIG. 23A depicts a male portion forming part of the adjustable offset rod-to-rod connector of FIG. 22. FIG. 23B depicts a female portion forming part of the adjustable offset rod-to-rod connector of FIG. 22. The adjustable offset rod-to-rod connector 1300 facilitates the adjacent engagement of a first elongated spinal rod 1302a and a second elongated spinal rod 1302b. The adjustable offset rod-to-rod connector 1300 includes a male portion 1304 and a female portion 1306 that are coupled such that the male and female portions 1304, 1306 may rotate with respect to each other. The male and female portions 1304, 1306 include a rod receiving hole 1308 for receiving the rods 1302a, 1302b therethrough and a set screw 1310 for locking the adjustable offset rod-to-rod connector 1300 to the rods 1302a, 1302b.

Figure 24:
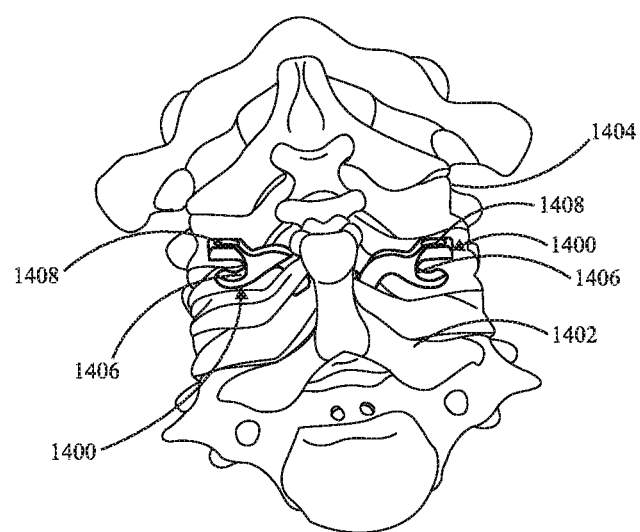
FIG. 24 is a perspective view of a side-loading laminar hook placed onto a lamina of a cervical vertebra forming part of a posterior cervical fixation system of FIG. 1.
Figure 25:
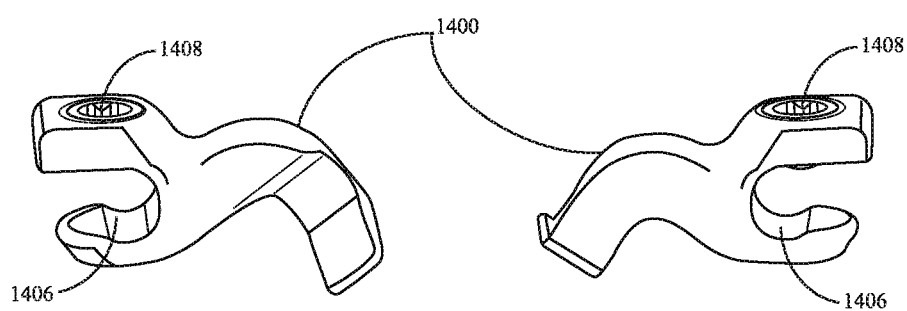
FIG. 25 is a side perspective view of a side-loading laminar hook of FIG. 24.
Figure 26:
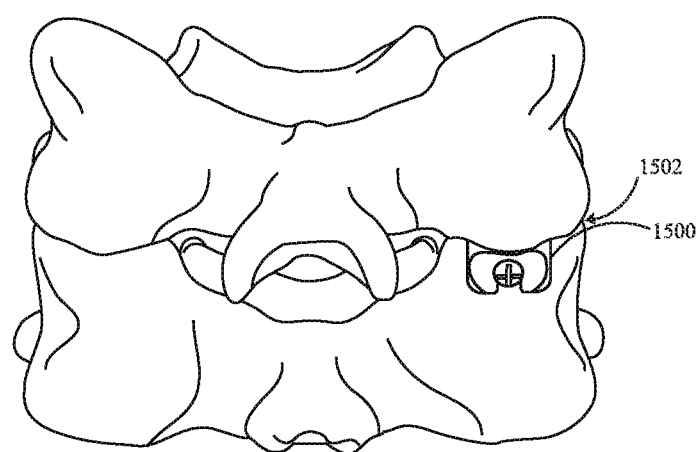
FIGS. 26 and 27 are perspective views of a facet spacer placed within a facet joint forming part of a posterior cervical fixation system of FIG. 1.
Figure 27:
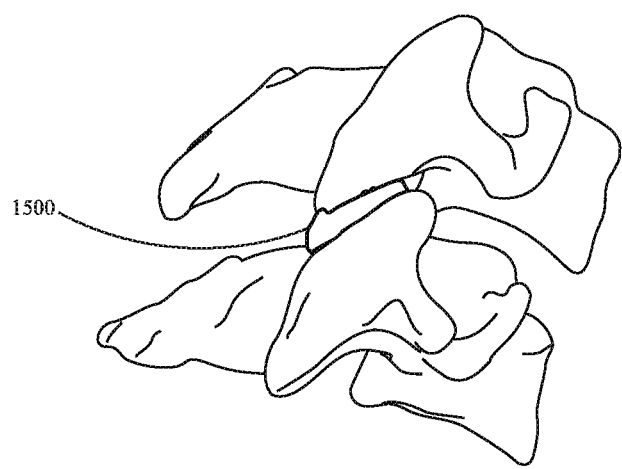
Figure 28:
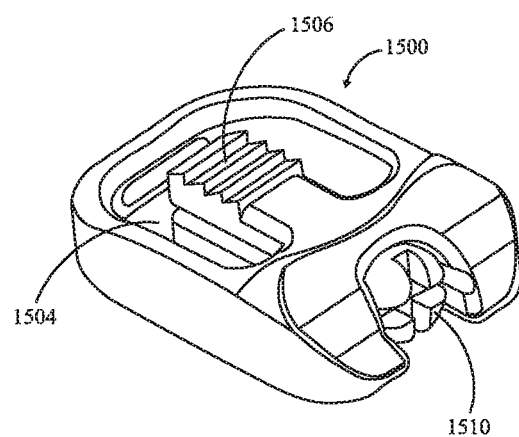
FIGS. 28-30 are front and perspective views, respectively, of the facet spacer of FIGS. 26 and 27, illustrating particularly a graft window, a deformable tab and a locking screw aperture.
Figure 29:
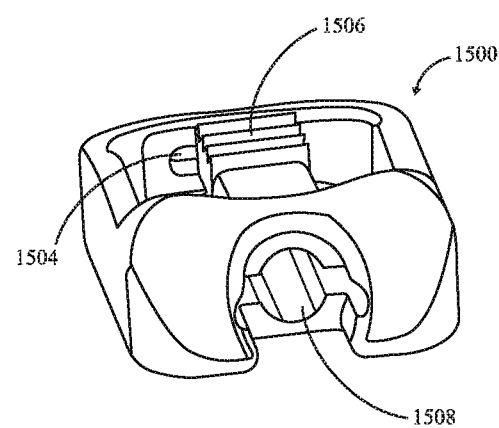

FIGS. 24 and 25 demonstrate one embodiment of a side-loading laminar hook forming part of a posterior cervical fixation system of FIG. 1. The side-loading laminar hook 1400 is dimensioned to hook onto a lamina 1402 of a cervical vertebra 1404. The side-loading laminar hook 1400 has a generally C-shaped rod-receiving portion 1406 for receiving spinal rods (not shown) therethrough. The first and second elongated spinal rods (not shown) are locked in place within the rod-receiving portion 1406 by a set screw 1408.

Figure 30:
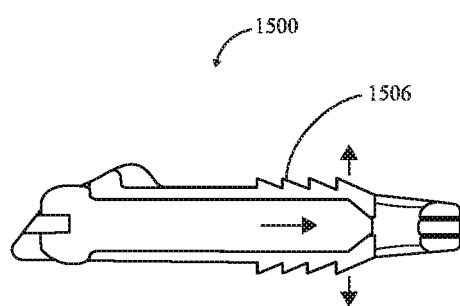

FIGS. 26-30 demonstrate one embodiment of a facet spacer forming part of a posterior cervical fixation system of FIG. 1. The facet spacer 1500 is dimensioned to be inserted into a facet joint 1502 of a vertebra. The facet spacer 1500 includes a graft window 1504 to allow bone growth therethrough to achieve fusion of the facet joint 1502 and a plurality of deformable tabs 1506 extending into the graft window 1504. The plurality of deformable tabs 1506 further includes teeth, which will engage the facet spacer 1500. The facet spacer 1500 includes a locking screw aperture 1508 for receiving a locking screw 1510. When the locking screw 1510 is inserted into the locking screw aperture 1508 of the facet spacer 1500, the plurality of deformable tabs 1506 urges apart (FIG. 30).

Figure 31:
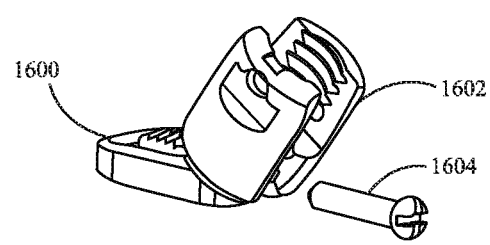
FIG. 31 is a perspective view of an alternative embodiment of the facet spacer of FIGS. 28-30.

FIG. 31 illustrates one embodiment of the facet spacer of FIGS. 26-30. The facet spacer 1600 in this embodiment is similar structurally and functionally to the embodiment described above in FIGS. 26-30, with a difference in that an anchor head 1602 is coupled to the facet spacer 1600. The anchor head 1602 is capable of receiving a spinal rod (not shown). The anchor head 1602 is attached to a locking screw 1604 which allows the adjustment of the position of the anchor head 1602 to a desired position for receiving the spinal rod (not shown). More particularly, the illustrated embodiment is similar in all other respects to the preferred embodiment described above, and as such similar components and features are numbered similarly, except in the 1600s rather than the 1500s.

Figure 32:
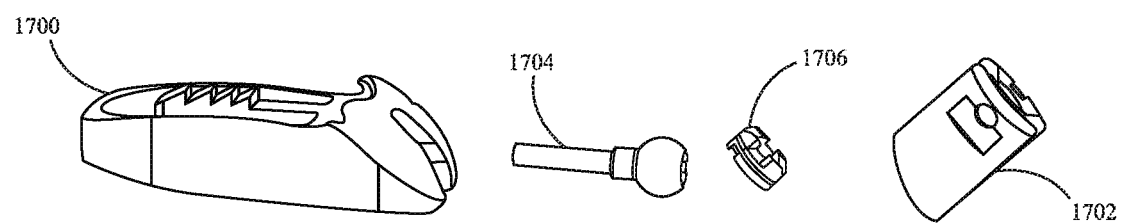
FIG. 32 is a perspective view of another embodiment of the facet spacer of FIGS. 28-30.

FIG. 32 illustrates yet another embodiment of the facet spacer of FIGS. 26-30. The facet spacer 1700 in this embodiment is similar structurally and functionally to the embodiment described above in FIGS. 26-30, with a difference in that an anchor head 1702 is attached to a locking screw 1704 that is having a spherical head 1706, allowing for adjustment of the position of the anchor head 1702 to a desired position for receiving a spinal rod (not shown). More particularly, the illustrated embodiment is similar in all other respects to the preferred embodiment described above, and as such similar components and features are numbered similarly, except in the 1700s rather than the 1600s.

FIGS. 33-35 demonstrate one embodiment of a multi-load polyaxial screw driver. The multi-load polyaxial screw driver 1800 having a distal end 1802 and a proximal end 1804. The multi-load polyaxial screw driver 1800 includes a handle 1806, an outer shaft 1808, inner shaft 1810, cartridge 1812 and slots for cartridge tab 1814. The outer shaft 1808 of the multi-load polyaxial screw driver 1800 can accommodate a plurality of polyaxial screws 1816. The cartridge 1812 include a hex-shaped end 1818 to mate to a hex-shaped recess 1828 in the anchor head 1826 of the polyaxial screw 1816 and a spherical tip 1820 proximal to the hex-shaped end 1818 that will engage the inside the hex-shaped recess 1828 of the anchor head 1826. Although shown as having a hex-shaped head in the exemplary embodiment, it will be appreciated that the cartridge may have a shaped end to complement the shape of any anchor head with which the multi-load polyaxial screw driver is used. The cartridge 1812 is coupled to each polyaxial screw 1816. The hex shaped end 1818 of the cartridge 1812 is engaged in the anchor head 1826 of one polyaxial screw 1816 and a screw shank 1830 of other polyaxial screw 1816 is engaged with a head 1824 of the cartridge 1812 and so on in a nested fashion. The cartridges 1812 further include side tabs 1822 that will engage slots 1814 in the outer shaft 1808 of the driver 1800 when the cartridge 1812 has been advanced to the distal end 1802 of the driver 1800 and the polyaxial screw engaged with that cartridge is exposed distally to the multi-load screwdriver. After the exposed polyaxial screw is deployed into the vertebral bone, the corresponding cartridge 1812 can then be pinched in at the side tabs 1822 and the empty cartridge 1812 along is released from the driver 1800. The cartridge 1812 can be removed from the outer shaft 1808 of the driver 1800 once the polyaxial screw 1816 has been driven into and secured in the spine. The head 1824 of the cartridge 1812 includes an aperture (not shown) for receiving the screw shank 1830 of the next polyaxial screw 1816. The inner shaft 1810 of the driver 1800 is spring-loaded which urges the plurality of polyaxial screws 1816 and the cartridges 1812 toward the distal end 1802 of the driver 1800.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An occipital cervical fixation system for securing a first spinal rod and a second spinal rod to spine, the occipital cervical fixation system comprising:
　an occipital plate member, comprising:
　　a main body portion having a first end opposite a second end and a centerline axis positioned between the first and second ends, and an aperture positioned along the centerline axis and configured to receive a bone anchor member;
　　a pair of rotatable housings configured to be coupled to the main body portion;
　　a pair of rod clamping elements that are each configured to translate medially and laterally within a respective one of the pair of rotatable housings, the pair of rod clamping elements comprising:
　　　a first rod clamping element disposed within a first rotatable housing of the pair of rotatable housings, wherein the first rod clamping element comprises a first clamp portion having a first U-shaped rod receiving end and a first hole extending therethrough, and
　　　a second rod clamping element disposed within a second rotatable housing of the pair of rotatable housings, wherein the second rod clamping element comprises a second clamp portion having a second U-shaped rod receiving end and a second hole extending therethrough,
　　　wherein the first U-shaped rod receiving end is configured to engage the first spinal rod and the second U-shaped rod receiving end is configured to engage the second spinal rod
　　　wherein a facet spacer that is configured for insertion into a facet joint of a vertebrae, the facet spacer including:
　　a graft window to enable bone growth therethrough;
　　a plurality of deformable tabs extending into the graft window; and
　　　a locking screw aperture configured to receive a locking screw that displaces the plurality of deformable tabs,
　　　wherein the facet spacer further comprises an anchor head that is configured to receive a third spinal rod.

2. The occipital cervical fixation system of claim 1, further comprising a multi-load polyaxial screwdriver configured to engage the bone anchor member.

3. The occipital cervical fixation system of claim 2, wherein the multi-load polyaxial screwdriver comprises:
　a distal end and a proximal end;
　a handle at the proximal end;
　an outer shaft between the handle and the distal end, the outer shaft having a slot therein;
　an inner shaft disposed within the outer shaft; and
　a cartridge disposed between the outer shaft and the distal end, the cartridge configured to engage the slot of the outer shaft when the cartridge is advanced to the distal end.

4. The occipital cervical fixation system of claim 3, wherein the cartridge of the multi-load polyaxial screwdriver further comprises:
    a keyed end configured to engage a complementary keyed recess in the bone anchor member for insertion into a bone; and
    a side tab configured to engage the slot of the outer shaft when the cartridge is advanced to the distal end.

* * * * *